United States Patent
Powers et al.

(10) Patent No.: US 11,801,172 B1
(45) Date of Patent: Oct. 31, 2023

(54) MINOR URINARY DISCHARGE CAPTURE (INCONTINENCE) DEVICE

(71) Applicant: Powers & Son, Inc., Allison Park, PA (US)

(72) Inventors: Michael Powers, Allison Park, PA (US); Larry Powers, Allison Park, PA (US)

(73) Assignee: Powers & Son, Inc., Allison Park, PA (US)

( * ) Notice: Subject to any disclaimer, the term of this patent is extended or adjusted under 35 U.S.C. 154(b) by 0 days.

(21) Appl. No.: 18/108,331

(22) Filed: Feb. 10, 2023

(51) Int. Cl.
| | | |
|---|---|---|
| *A61F 13/471* | (2006.01) | |
| *A61F 5/453* | (2006.01) | |
| *A61F 13/47* | (2006.01) | |
| *A61F 13/15* | (2006.01) | |
| *A61F 13/45* | (2006.01) | |

(52) U.S. Cl.
CPC ............ *A61F 13/471* (2013.01); *A61F 5/453* (2013.01); *A61F 13/15739* (2013.01); *A61F 13/4704* (2013.01); *A61F 2013/4506* (2013.01)

(58) Field of Classification Search
CPC .......... A61F 5/44; A61F 5/4401; A61F 5/443; A61F 5/451; A61F 5/453; A61F 13/45; A61F 13/4704; A61F 13/471; A61F 2013/4506; A61F 2013/4512
See application file for complete search history.

(56) References Cited

U.S. PATENT DOCUMENTS

| | | | | |
|---|---|---|---|---|
| 5,735,837 A | * | 4/1998 | Ishikawa | A61F 5/453 604/352 |
| 5,827,250 A | * | 10/1998 | Fujioka | A61F 5/4401 604/385.19 |
| 6,129,719 A | * | 10/2000 | Nozaki | A61F 13/471 604/385.01 |
| 6,530,909 B1 | * | 3/2003 | Nozaki | A61F 13/471 604/349 |
| 2005/0015067 A1 | * | 1/2005 | Suzuki | A61F 13/551 604/385.02 |
| 2006/0149196 A1 | * | 7/2006 | Bjornberg | A61F 5/453 604/349 |
| 2011/0015604 A1 | * | 1/2011 | Back | A61F 13/471 604/385.03 |
| 2012/0046633 A1 | * | 2/2012 | Okawa | A61F 13/471 604/385.24 |

\* cited by examiner

*Primary Examiner* — Catharine L Anderson
(74) *Attorney, Agent, or Firm* — Michael Best & Friedrich LLP

(57) ABSTRACT

A product for mitigating the ill-effects of post-coital discharge, post-medical-procedure discharge, and post-urination discharge in men. A sleeve-like pouch includes an inside and an outside, with a top layer disposed on the inside of the sleeve-like pouch, and a bottom layer disposed on the outside of the sleeve-like pouch. An absorbent layer is disposed between the top layer and bottom layer. The sleeve-like pouch is configured to be slid onto and securely surround a male appendage.

20 Claims, 5 Drawing Sheets

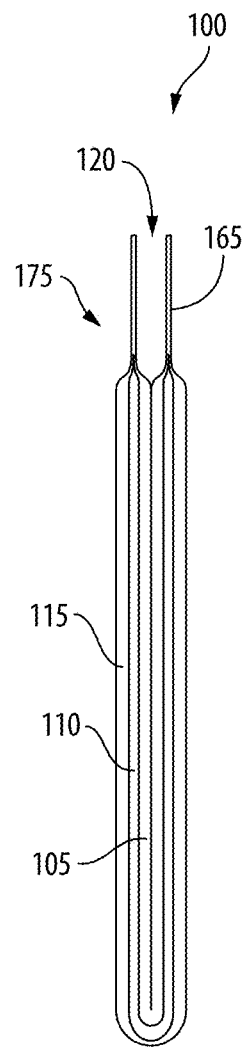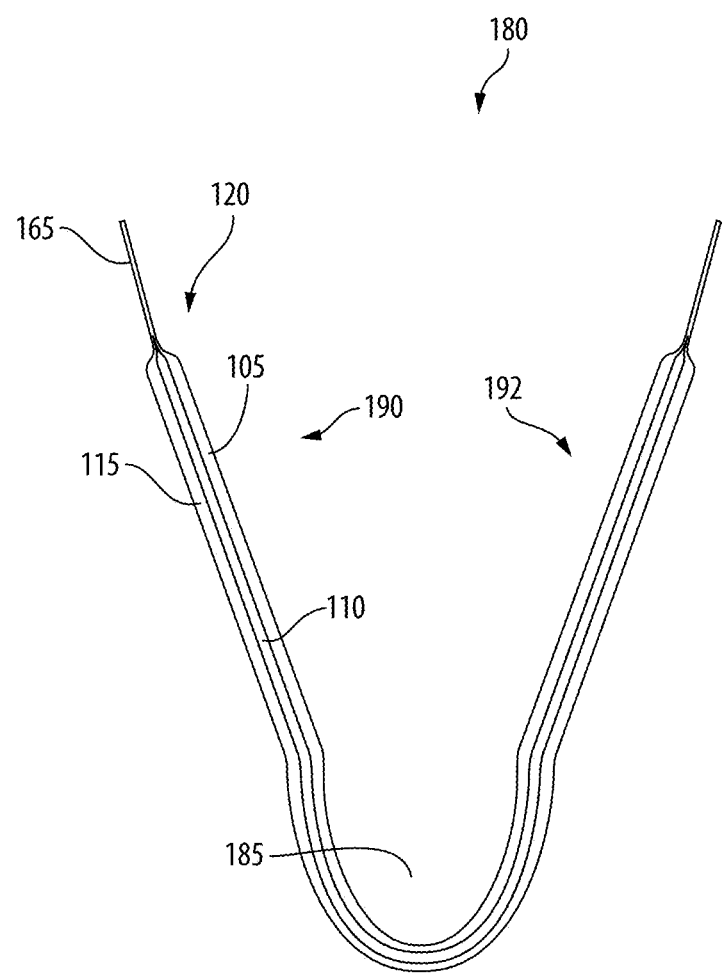
Fig. 1D                    Fig. 1E

MINOR URINARY DISCHARGE CAPTURE (INCONTINENCE) DEVICE

FIELD

The embodiments disclosed herein relate to methods and products for addressing minor male incontinence (e.g., post-urination discharge) in men.

BACKGROUND

Post-urination discharge becomes an issue for men as they age. This problem is acute among men with prostate and bladder-sensitivity conditions, which are becoming more prevalent as each generation lives longer. Additionally, pos-coital discharge and post-medical-procedure discharge in men can lead to unsightly marks on clothing.

SUMMARY

This document discloses several products configured to address problems like post-coital discharge, post-medical-procedure discharge, and minor male incontinence like post-urinary discharge in men. In an embodiment, a sleeve-like pouch is made of absorbent, non-woven material configured to be slipped onto the male appendage. The pouch may be disposable, and may include a liquid-proof outer barrier configured prevent any delayed/unwanted/minor post-urination discharge from passing through an absorbent layer of the pouch into a garment of a user. After use, the user may remove and dispose of the absorbent pouch at their convenience. The pouch may be packaged in a flat, folded, closed configuration but is configured to unfold into an opened configuration for use. The dimensions of the pouch may be small enough so that, in the closed configuration, multiple pouches can be carried in a pocket or wallet of a user for convenient use throughout the day. In this way, the disposable pouch may be carried discretely, used conveniently as a receptacle for post urination discharge to address minor male incontinence, and disposed of discretely.

In an embodiment, a sleeve-like pouch includes an inside and an outside. The sleeve-like pouch also includes a top layer disposed on the inside of the sleeve-like pouch and a bottom layer disposed on the outside of the sleeve-like pouch. An absorbent layer disposed between the top layer and bottom layer. The sleeve-like pouch is configured to be slid onto and securely surround a male appendage.

In another embodiment, an absorbent pad includes a top layer, a bottom layer sealed against the top layer, and one or more tabs disposed at one or more longitudinal ends of the absorbent pad. The absorbent pad also includes a first lateral side, a second lateral side, and a folding portion, wherein the absorbent pad is configured to be folded back onto itself at the folding portion to form a sleeve-like pouch when the first lateral side is sealed against itself, and the second lateral side is sealed against itself.

In another embodiment, a method of producing a sleeve-like pouch out of an absorbent pad includes selecting an absorbent pad sized an shaped to be slid onto an end of a human appendage after being folded folding the absorbent pad upon itself such that a first lateral side of the absorbent pad overlays itself and a second lateral side of the absorbent pad overlays itself, adhering the first lateral side to itself; and adhering the second lateral side to itself to form the sleeve-like pouch.

Other aspects of the technology will become apparent by consideration of the detailed description and accompanying drawings.

BRIEF DESCRIPTION OF THE DRAWINGS

FIG. 1D depicts a sectional lateral view of the sleeve-like pouch in a folded, closed configuration according to an embodiment.

FIG. 1E depicts a sectional lateral view of the sleeve-like pouch in an unfolded, opened configuration according to an embodiment.

DETAILED DESCRIPTION

Before any embodiments of the application are explained in detail, it is to be understood that the application is not limited in its application to the details of construction and the arrangement of components set forth in the following description or illustrated in the following drawings. The application is capable of other embodiments and of being practiced or of being carried out in various ways.

Also, it is to be understood that the phraseology and terminology used herein are for the purpose of description and should not be regarded as limiting. The use of "including," "comprising," or "having" and variations thereof are meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. As used within this document, the word "or" may mean inclusive or. As a non-limiting example, if it we stated in this document that "item Z may comprise element A or B," this may be interpreted to disclose an item Z comprising only element A, an item Z comprising only element B, as well as an item Z comprising elements A and B.

Figure 1A:
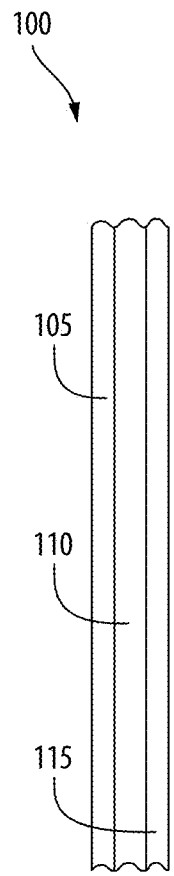
FIG. 1A depicts several layers of an absorbent pad.
Figure 1B:
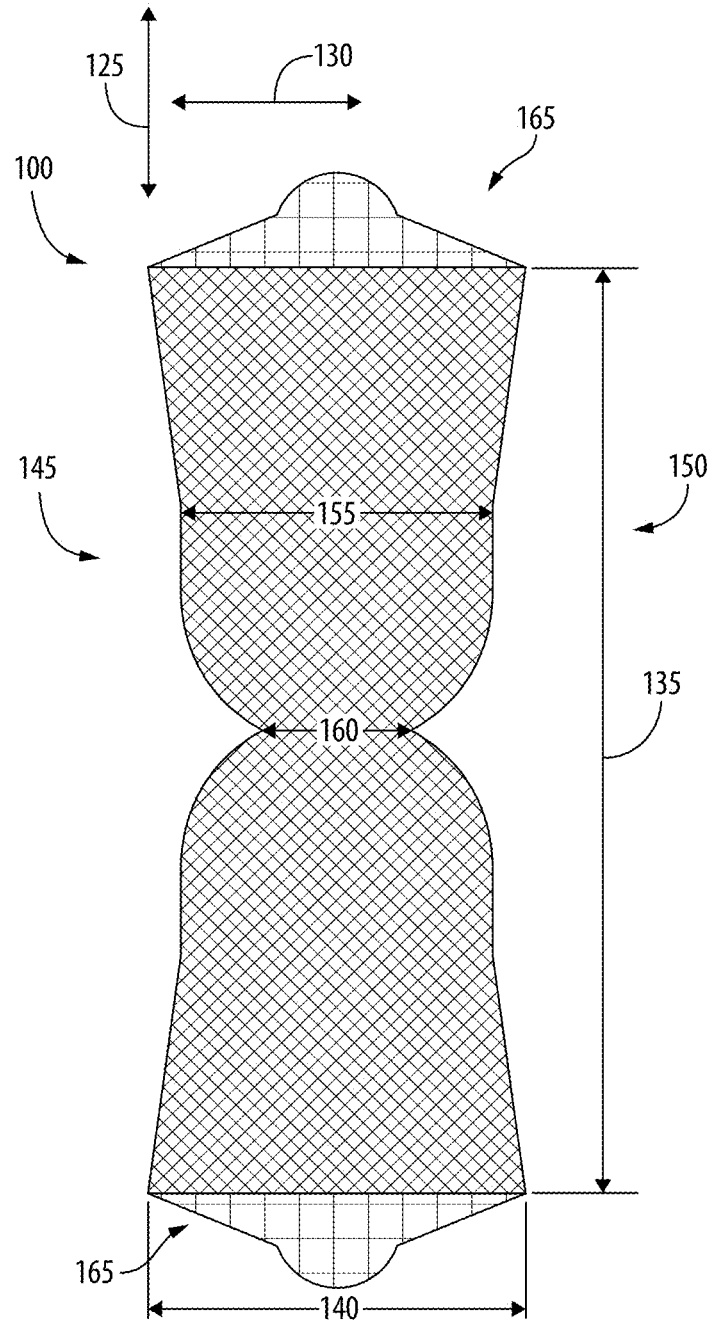
FIG. 1B depicts a front view of a sleeve-like pouch, constructed from the absorbent pad and arranged in a pre-folded configuration according to an embodiment.

FIGS. 1A and 1B illustrate an absorbent pad 100 configured to absorb fluid (e.g., water, bodily fluid, etc.). FIG. 1A shows that the absorbent pad 100 includes a top layer 105, an absorbent layer 110, and a bottom layer 115. In the embodiment shown, the top layer 105 is constructed from a fluid permeable material that allows fluid to pass through to the absorbent layer 110 to be absorbed. For example, the top layer 105 may be constructed of a porous material, or pores or perforations may be made in a non-porous material to produce the top layer 105. The top layer 105 may be configured to retain very little fluid as compared to the absorbent layer 110. The top layer 105 may also be constructed of a non-irritative material or configured to avoid or prevent irritation to human skin.

The absorbent layer 110 is disposed between the top layer 105 and the bottom layer 115. In some embodiments, the absorbent layer is sealed against the top layer 105 and/or bottom layer 115 by using an adhesive, a heat sealing process, or some other bonding method. In some embodiments, the top layer 105 is sealed against the back sheet 110 such that the top layer 105 and the bottom layer 115 encapsulate the absorbent layer 110. For example, the top layer 105 and bottom layer 115 may be larger in width and height than the bottom layer 115, and sealed against one another, directly or indirectly, at one or more edges of the bottom layer 115. Further, the absorbent layer 110 may be configured to absorb any fluids (e.g., bodily fluids) that pass through the top layer 105. The absorbent layer 110 may include an anti-odor or odor-capturing agent configured to mitigate any odors from the absorbed fluid emanating back out from the absorbent layer 110. The absorbent layer 110 may include one or more layers of absorbent material and may include a plurality of fluid absorbing elements. The absorbent layer 110 may be constructed of organic or synthetic hydrophilic or superabsorbent material. For example, the absorbent layer 110 may include plant material (e.g., cellulose, cotton, wood pulp fibers), polymers (e.g., hydrogel forming polymers), or other non-synthetic or synthetic hydrophilic or superabsorbent materials. In some embodiments, the absorbent layer 110 includes a combination of distinct absorbent materials (e.g., an absorbent layer including a sublayer of cotton, a sublayer of cellulose, and a sublayer of hydrogel forming polymer).

The bottom layer 115 is generally liquid impermeable. For example, the bottom layer 115 may include a liquid impermeable sublayer or coating configured to prevent fluid not absorbed by the absorbent layer 110 from leaking through the absorbent pad 100 and onto something beyond the absorbent pad 100 (e.g., a user's undergarments). In this way, the bottom layer 115 may be configured to act as a barrier for liquids. The bottom layer 115 may be made of a liquid impermeable synthetic material (e.g., a non-woven polymer) or a non-synthetic material treated with a sealing agent or a hydrophobic agent (e.g., a cotton layer coated in wax).

Although the absorbent pad 100 is often illustrated herein as including a top layer 105, an absorbent layer 110, and a bottom layer 115, it is contemplated that the absorbent may include fewer or additional layers. For example, in some embodiments, the absorbent pad 100 includes only a top layer 105 and a bottom layer 115. Additionally, it is contemplated that top layer 105, absorbent layer 110, and bottom layer 115, may each perform mixed functions, as desired. For example, in an embodiment wherein the absorbent pad includes only a top layer 105 and a bottom layer 115, the top layer 105 may be configured to have properties similar to those of both the top layer and the absorbent layer as described above (e.g., comfort, superabsorbancy, and odor capture). It is also contemplated that one or more of the top layer 105, absorbent layer 110, or bottom layer 115 may be sealed against one another.

FIG. 1B illustrates a front view of an absorbent pad 100 is sized and shaped for folding into a sleeve-like pouch for a male appendage. The measurements described in reference to FIG. 1B are merely intended to be illustrative and not limiting. It is contemplated that the absorbent pad 100 may have different measurements and a different shape in other embodiments to produce a variety of desirable traits (e.g., discreteness, fit, etc.). In the embodiment shown, the absorbent pad 100 includes a longitudinal direction 125 and a lateral direction 130. The absorbent pad 100 also includes a pad length 135 and a pad width 140, a first lateral side 145 and a second lateral side 150. The pad width 140 may change along the pad length 135. In the embodiment shown, the pad width 140 is 3 inches and the pad length 135 is 7.5 inches. The pad width 140 tapers down along the first 1.85 inches of the absorbent pad 100 until a reduced pad width 155 of 2.45 inches is reached. Also, in the embodiment shown, the pad width 140 further reduces until a width of 1.2 inches is reached at a folding portion 160. The folding portion 160 is therefore located generally at a halfway point along the pad length 135.

The absorbent pad is configured to be folded at the folding portion 160 and adhered upon itself along the first lateral side 145 and the second lateral side 150 to form a receptacle in the form of sleeve-like pouch. The sleeve-like pouch may be configured to be slid onto and securely retained on a male appendage to act as a receptacle for post-urination discharge. One or more tabs 165 may be disposed at the longitudinal ends of the absorbent pad 100 and configured to facilitate a user grabbing and pulling on the tabs 165 to manipulate the absorbent pad for easier placement and adjustment on the male appendage.

Although the sleeve-like pouch is illustrated in the figures as being an absorbent pad 100 folded on itself in a particular manner and adhered along its first lateral side 145 and second lateral side 150, it is contemplated that a sleeve-like pouch could be formed by other means. For example, a sleeve-like pouch could be formed by adhering two appropriately sized and shaped absorbent pads together along their edges to form an absorbent pouch.

Figure 1C:
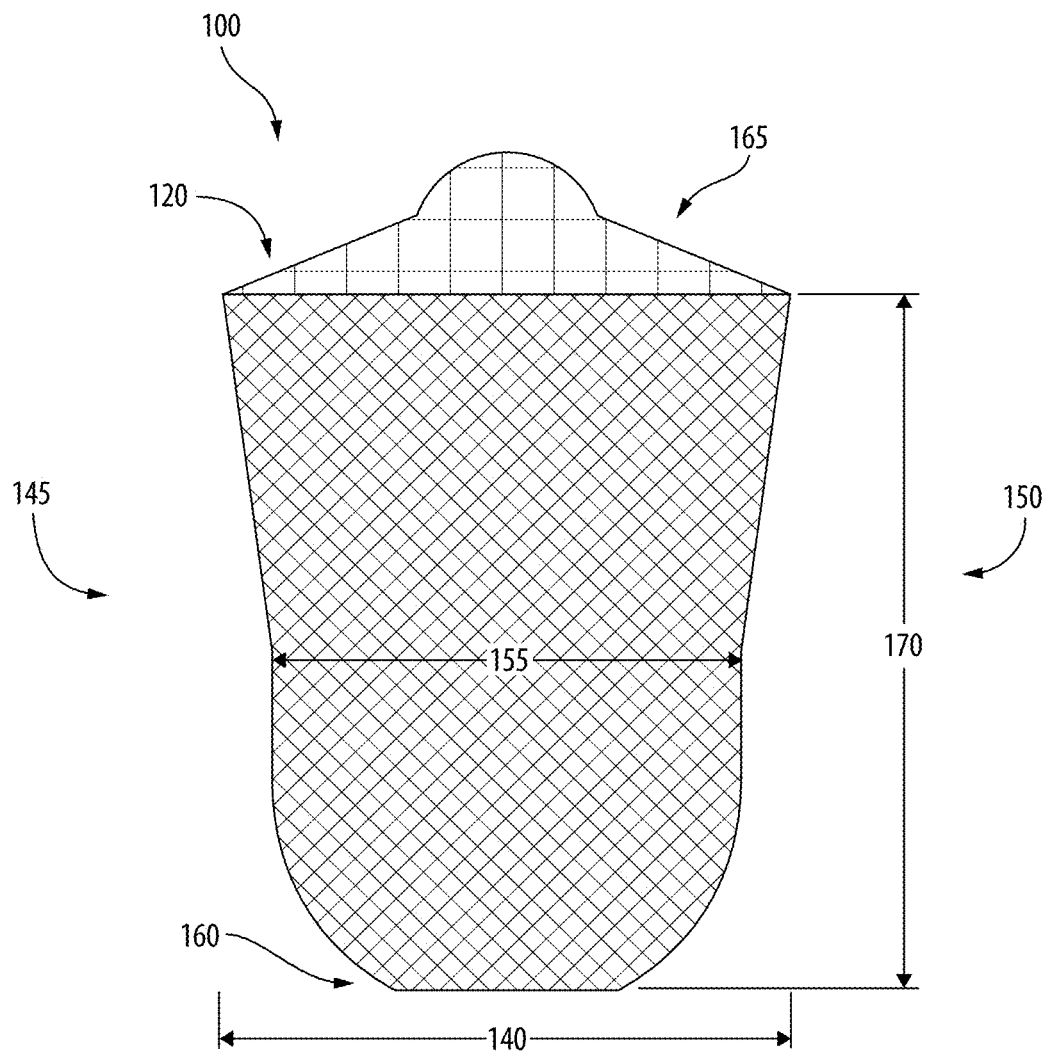
FIG. 1C depicts a front view of the sleeve-like pouch in a folded, closed configuration according to an embodiment.

FIG. 1C illustrates an embodiment wherein the absorbent pad 100 is folded into a sleeve-like pouch 120. The absorbent pad is folded at folding portion 160 and onto itself. The absorbent pad 100, being folded generally in half, has pouch length 170. In the embodiment shown, the pouch length 170 is 3.75 inches, but the pouch may have a different length. The first lateral side 145 is folded back on itself and sealed against itself along its edge forming a first side seam (not shown). Likewise, the second lateral side 150 is folded back on itself and adhered along its edge forming a second side seam (not shown). In the embodiment shown, the folding portion 160 of the absorbent pad 100 acts as the bottom of the sleeve-like pouch 120, and when the absorbent pad 100 is folded, the one or more tabs 165 are disposed at the top of the sleeve-like pouch 120.

FIG. 1D illustrates a side sectional view of the sleeve-like pouch 120 of FIG. 1C constructed from the absorbent pad 100 folded into a folded closed configuration 175. Here, absorbent pad 100 is folded into a sleeve-like pouch 120 having 3-layers. However, as described previously, the absorbent pad may only include two layers (e.g., an absorbent layer 110 and a bottom layer 115, a top layer 105 and a bottom layer 115, etc.). The top layer 105 generally overlays and abuts itself 105 in the folded closed configuration 175, while the bottom layer 115 surrounds both the top layer 105 and the absorbent layer. The first and second lateral sides (not shown) are adhered upon themselves as described above so as to prevent any fluid entering the sleeve-like pouch 120 from flowing out of the sleeve-like pouch 120 at the first and second lateral sides (not shown).

FIG. 1E illustrates a side sectional view of the sleeve-like pouch 120 of FIG. 1C in an unfolded opened configuration 180. In this configuration, the first and second lateral sides (not shown) remain adhered upon themselves, and folding portion 160 is unfolded to a degree that causes a cavity 185 to form between a front 190 and a back 192 of the sleeve-like pouch. The cavity 185 is configured to accommodate a portion of a human body part (e.g., a male appendage), to absorb fluid (e.g., bodily fluid, urine, etc.) from that body part, and to prevent the absorbed fluid from making its way out of the sleeve-like pouch 120. For example, the sleeve-like pouch 120 in the unfolded opened configuration 180 may be slid onto the end of a male appendage after urination in order to collect post-urination discharge at least in the top layer 105 at the cavity 185, the front 190 or back 192 of the sleeve-like pouch 120, or in the first and second lateral sides (not shown).

Figure 2A:
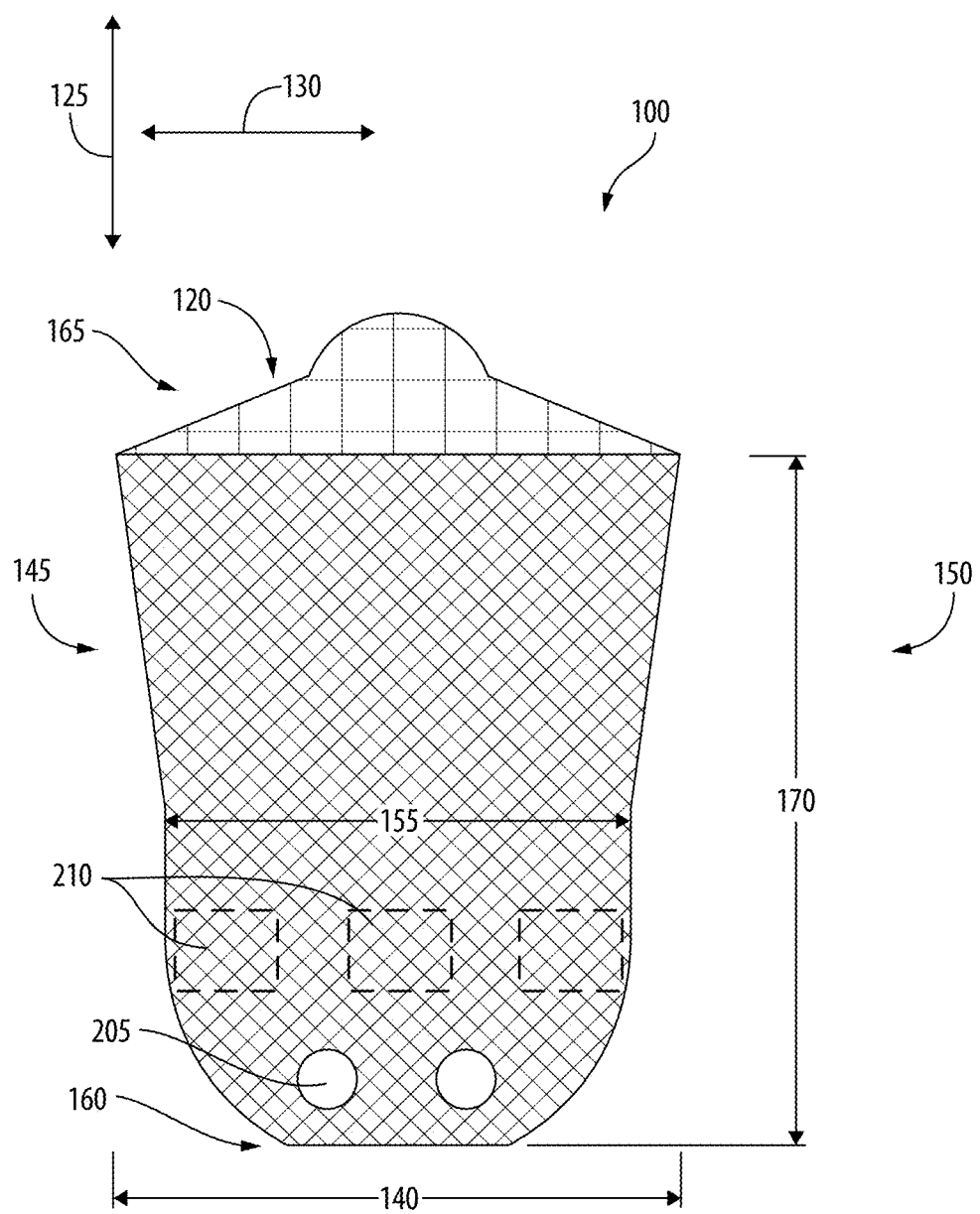
FIG. 2A depicts a front view of a sleeve-like pouch in a folded, closed configuration according to an embodiment.

FIG. 2A illustrates a front view of another embodiment the sleeve-like pouch 120. Outer retention elements 205 are disposed on the outside of the sleeve-like pouch 120, and inner retention elements 210 disposed on the inside of the sleeve-like pouch 120. In the embodiment shown, the inner retention elements 210 are configured to retain the sleeve-like pouch 120 on a human body part inserted into the sleeve-like pouch 120. In this way, the sleeve-like pouch 120 may act as a receptacle for a human body part (e.g., the male appendage). The outer retention elements 205 or configured to prevent or mitigate the movement of the sleeve-like pouch 120 within a garment (e.g., undergarments) of a user of the sleeve-like pouch 120. The outer retention elements 205 and the inner retention elements 210 may be constructed of any lightly tacky or lightly sticky material. For example, the outer retention elements 205 and inner retention elements 210 may be segments of light adhesive, tape, wax, silicone, etc.

Figure 2B:
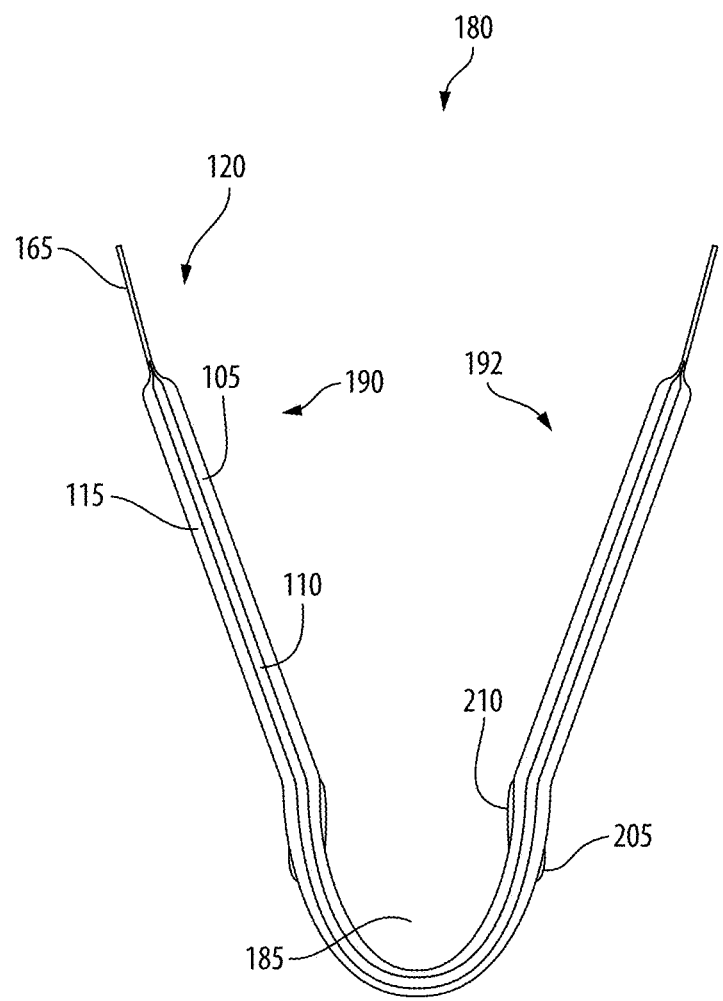
FIG. 2B depicts a sectional lateral view of the sleeve-like pouch in an unfolded, opened configuration according to an embodiment.

FIG. 2B illustrates a side sectional view of the sleeve-like pouch 120 of FIG. 2A in a unfolded opened configuration 180. In the embodiment shown, the inner retention elements 210 are disposed inside of the cavity 185, and the outer retention elements 205 are disposed on the outside of the cavity 185. The inner retention elements 210 may gently adhere to a body part placed into the sleeve-like pouch 120, while the outer retention elements 205 stabilize the sleeve-like pouch 120 against a garment of a user, for example, to prevent friction between the user and the sleeve-like pouch. It is contemplated that elastic bands or other means may also be used for retention of a human body part within the sleeve-like pouch.

The absorbent pad 100 and sleeve-like pouch 120 herein are described to have a fairly particular shape for a specific human appendage. However, it is contemplated that the absorbent pad 100 and the sleeve-like pouch 120 may have different shapes and sizes for varying uses (e.g., post-surgical fluid collection) with other appendages (e.g., a finger). It is also contemplated that the absorbent pad may have more or less layers than shown and that distinct absorbent pads can be sealed against one another at their edges to form a sleeve-like pouch. For example, a 1-layer absorbent pad may be sealed against a three-layer absorbent pad to form a sleeve-like pouch for the uses described herein.

Various features and advantages of the invention are set forth in the following claims.

What is claimed is:

1. A product comprising:
    a sleeve-like pouch having an inside and an outside, including
        a top layer disposed on the inside of the sleeve-like pouch,
        a bottom layer disposed on the outside of the sleeve-like pouch,
        an absorbent layer disposed between the top layer and bottom layer,
        a first tab disposed on a front side of the sleeve-like pouch, and
        a second tab disposed on a back side of the sleeve-like pouch,
        wherein the first tab and second tab are configured to allow a user to manipulate the sleeve-like pouch for pulling over an appendage of the user, and
        wherein the sleeve-like pouch is configured to be slid onto and securely surround a male appendage.

2. The product of claim 1, wherein the sleeve-like pouch includes a first side seam and a second side seam, and a folded bottom portion.

3. The product of claim 2, wherein the sleeve-like pouch is configured to be stored flat, in a folded closed configuration, and unfolded into an unfolded opened configuration for use.

4. The product of claim 1, wherein the sleeve-like pouch includes retention elements disposed on the top layer of the sleeve-like pouch.

5. The product of claim 1, wherein the sleeve-like pouch incudes retention elements disposed on the bottom layer of the sleeve-like pouch.

6. The product of claim 1, wherein the top layer is made of a non-woven material.

7. The product of claim 1, wherein the bottom layer is made of a liquid impermeable material.

8. A product comprising:
    an absorbent pad including
        a top layer,
        a bottom layer sealed against the top layer,
        a first tab disposed on a first longitudinal end of the absorbent pad, and
        a second tab disposed on a second longitudinal end of the absorbent pad,
        a first lateral side,
        a second lateral side, and,
        a folding portion;
        wherein the absorbent pad is configured to be folded back onto itself at the folding portion to form a sleeve-like pouch when
            the first lateral side is sealed against itself, and
            the second lateral side is sealed against itself, and
        wherein the first tab and second tab are configured to allow a user to manipulate the sleeve-like pouch for pulling over an appendage of the user.

9. The product of claim 8, wherein the sleeve-like pouch includes a first side seam and a second side seam, and a folded bottom portion.

10. The product of claim 9, wherein the sleeve-like pouch is configured to be stored flat, in a folded closed configuration, and unfolded into an unfolded opened configuration for use.

11. The product of claim 8, wherein the absorbent pad includes retention elements disposed on the top layer.

12. The product of claim 8, wherein the absorbent pad incudes retention elements disposed on the bottom layer.

13. The product of claim 8, wherein the top layer is made of a non-woven material.

14. The product of claim 8, wherein the bottom layer is made of a liquid impermeable material.

15. A method of producing a sleeve-like pouch out of an absorbent pad comprising:
    selecting an absorbent pad sized an shaped to be slid onto an end of a human appendage after being folded to produce the sleeve-like pouch;
    folding the absorbent pad upon itself such that a first lateral side of the absorbent pad overlays itself and a second lateral side of the absorbent pad overlays itself;
    adhering the first lateral side to itself; and,
    adhering the second lateral side to itself, wherein the sleeve-like pouch includes a first tab disposed on a front side of the sleeve-like pouch, and a second tab disposed on a back side of the sleeve-like pouch, and wherein the tabs are configured to allow a user to manipulate the sleeve-like pouch for pulling over an appendage of the user.

16. The method of claim 15, wherein the absorbent pad is sized to be stored in a wallet of the user.

17. The method of claim 15, wherein a pouch length of the absorbent pad is 3.75 inches.

18. The method of claim 15, wherein a width of the absorbent pad at its widest point is 3 inches.

19. The method of claim 15, wherein a width of the absorbent pad at its narrowest point is 1.2 inches.

20. The method of claim 15, wherein the absorbent pad includes a fluid permeable top layer and a fluid impermeable bottom layer.

* * * * *